US007393874B2

(12) United States Patent
Reddy et al.

(10) Patent No.: US 7,393,874 B2
(45) Date of Patent: Jul. 1, 2008

(54) POLYMORPHS OF TOLTERODINE TARTRATE

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN); Kesireddy Subash Chander Reddy, Hyderabad (IN)

(73) Assignee: Hetero Drugs Limited, Hyderabad (IN)

( * ) Notice: Subject to any disclaimer, the term of this patent is extended or adjusted under 35 U.S.C. 154(b) by 639 days.

(21) Appl. No.: 10/510,435

(22) PCT Filed: Apr. 8, 2003

(86) PCT No.: PCT/IN03/00149

§ 371 (c)(1),
(2), (4) Date: Oct. 6, 2004

(87) PCT Pub. No.: WO2004/089281

PCT Pub. Date: Oct. 21, 2004

(65) Prior Publication Data

US 2005/0131067 A1    Jun. 16, 2005

(51) Int. Cl.
*A61K 31/135* (2006.01)
*C07C 215/54* (2006.01)

(52) U.S. Cl. .................................. 514/648; 564/316
(58) Field of Classification Search ................ 564/316; 514/648
See application file for complete search history.

(56) References Cited

U.S. PATENT DOCUMENTS 5,922,914 A    7/1999  Gage et al.
7,005,449 B2 *  2/2006  Hawley et al. ............. 514/555

FOREIGN PATENT DOCUMENTS

EP    325 571 A1    7/1989

OTHER PUBLICATIONS

PCT International Search Report Dated Apr. 8, 2003.

* cited by examiner

*Primary Examiner*—Peter G O'Sullivan
(74) *Attorney, Agent, or Firm*—Caesar, Rivise, Bernstein, Cohen & Pokotilow, Ltd.

(57) ABSTRACT

The present invention relates to novel polymorphs of tolterodine tartrate, to processes for their preparation and to pharmaceutical compositions containing them.

28 Claims, 5 Drawing Sheets

POLYMORPHS OF TOLTERODINE TARTRATE

FIELD OF THE INVENTION

This application is a 371 of PCT/IN03/00149 filed 8 Apr. 2003.

The present invention relates to novel polymorphs of tolterodine tartrate, to processes for their preparation and to pharmaceutical compositions containing them.

BACKGROUND OF THE INVENTION

Tolterodine of formula (1):

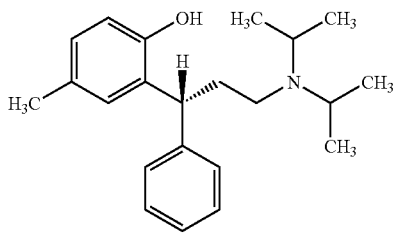

or 2-[(1R)-3-[bis(1-methylethyl)amino]-1-phenylpropyl]-4-methylphenol and its salts are muscarinic receptor antagonists. Tolterodine tartrate is a muscarinic receptor antagonist and is used in the treatment of urinary incontinence. Tolterodine tartrate and related compounds and their therapeutic uses are disclosed in EP 0325571.

Polymorphs of tolterodine tartrate were not reported in the literature. So, there is a need for stable, well-defined and reproducible crystalline forms.

It has now been discovered that tolterodine tartrate can be prepared in four well-defined and consistently reproducible crystalline forms and one stable amorphous form.

The object of the present invention is to provide stable novel polymorphs of tolterodine tartrate, processes for preparing these forms and pharmaceutical compositions containing them.

DETAILED DESCRIPTION OF THE INVENTION

In accordance with the present invention, there is provided a novel crystalline form of tolterodine tartrate, designated as form I, characterized by an x-ray powder diffraction spectrum having peaks expressed as 2θ at about 11.9, 13.6, 14.2, 15.9, 16.9, 18.4, 18.8, 20.4, 22.0, 23.9, 25.4, 26.3 and 29.8 degrees. FIG. 1 shows typical form I x-ray powder diffraction spectrum.

In accordance with the present invention, a process is provided for preparation of tolterodine tartrate form I. Thus, tolterodine free base is dissolved in a suitable solvent, tartaric acid is added to the solution and tolterodine tartrate form I is isolated. The suitable solvents are ethanol, methylene dichloride, chloroform, acetone, acetonitrile and 1,4-dioxane; and a mixture thereof. The preferable solvents are ethanol and acetone.

In accordance with the present invention, there is provided a novel crystalline form of tolterodine tartrate, designated as form II, characterized by an x-ray powder diffraction spectrum having peaks expressed as 2θ at about 8.7, 9.0, 9.6, 10.1, 10.4, 11.9, 14.0, 15.7, 16.9, 17.6, 17.9, 18.4, 18.7, 20.0, 20.5, 22.1, 24.5, 29.1 and 35.9 degrees. FIG. 2 shows typical form II x-ray powder diffraction spectrum.

In accordance with the present invention, a process is provided for preparation of tolterodine tartrate form II. Thus, tolterodine free base is dissolved in ethyl acetate, tartaric acid is added and tolterodine tartrate form II is isolated by filtration or centrifugation.

In accordance with the present invention, there is provided a novel crystalline form of tolterodine tartrate, designated as form III, characterized by an x-ray powder diffraction spectrum having peaks expressed as 2θ at about 9.1, 9.7, 10.6, 11.7, 11.9, 12.7, 14.3, 15.7, 17.9, 18.5, 18.8, 19.1, 20.1, 20.4, 22.1, 22.5, 25.1, 32.8 and 35.5 degrees. FIG. 3 shows typical form III x-ray powder diffraction spectrum.

In accordance with the present invention, a process is provided for preparation of tolterodine tartrate form III. Thus, tolterodine free base is dissolved in methyl tert-butyl ether, tartaric acid is added to the solution and tolterodine tartrate form III is isolated by filtration or centrifugation.

In accordance with the present invention, there is provided a novel crystalline form of tolterodine tartrate, designated as form IV, characterized by an x-ray powder diffraction spectrum having peaks expressed as 2θ at about 7.8, 9.8, 15.2, 17.2, 17.7, 18.4, 18.9, 20.3 and 25.9 degrees. FIG. 4 shows typical form IV x-ray powder diffraction spectrum.

In accordance with the present invention, a process is provided for preparation of tolterodine tartrate form IV. Thus, tolterodine tartrate, an alcohol and water are mixed and the solvents are removed from the solution by freeze drying. The suitable alcohols are methanol, ethanol, isopropyl alcohol and n-butanol; and a mixture thereof. The preferable alcohols are methanol and ethanol.

In accordance with the present invention, there is provided a novel amorphous form of tolterodine tartrate, designated as amorphous tolterodine tartrate, characterized by having broad x-ray diffraction spectrum as in FIG. 5.

In accordance with the present invention, a process is provided for preparation of amorphous tolterodine tartrate. Thus, tolterodine tartrate, an alcohol and water are mixed and the solvents are removed from the solution by vacuum drying or spray drying. The suitable alcohols are methanol, ethanol, isopropyl alcohol and n-butanol; and a mixture thereof. The preferable alcohol are methanol and ethanol.

Tolterodine free base and tolterodine tartrate used in the above processes can be obtained from the previously known methods.

In accordance with the present invention, there is provided a pharmaceutical composition comprising a polymorphic form of tolterodine tartrate and pharmaceutically acceptable carrier or diluent. The polymorphic form includes form I, form II, form III, form IV or amorphous tolterodine tartrate.

Figure 1:
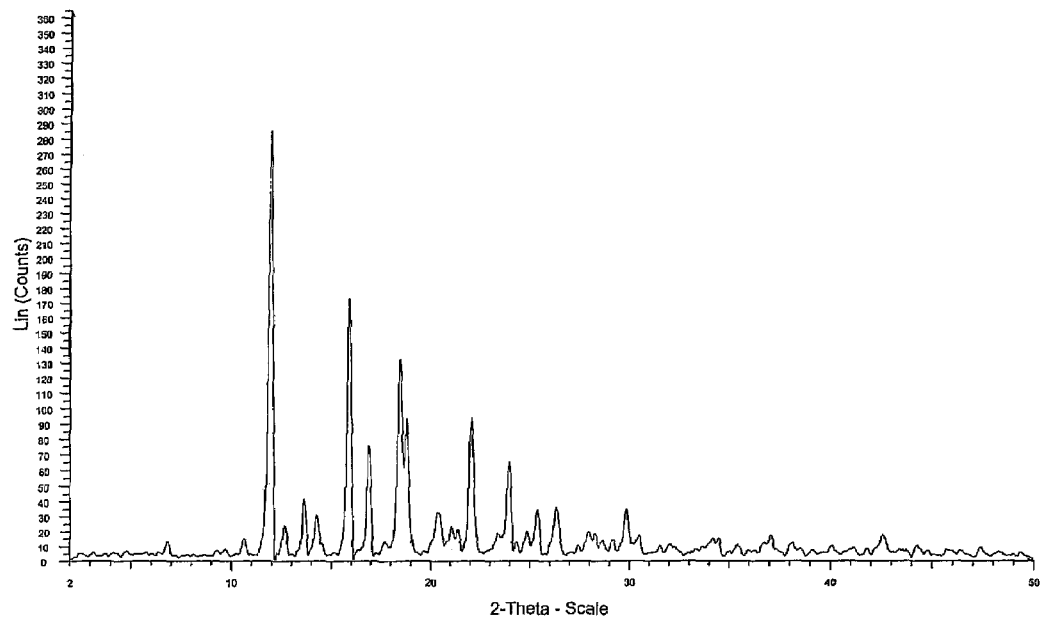
FIG. 1 is a x-ray powder diffraction spectrum of tolterodine tartrate form I.

x-Ray powder diffraction spectrum was measured on a Siemens D5000 x-ray powder diffractometer having a copper-Kα radiation.

The following examples further illustrate the present invention.

EXAMPLE 1

Tolterodine free base (5.0 gm) is dissolved in ethanol (75 ml) and tartaric acid (3.0 gm) is added to the solution. Then the contents are stirred for 2 hours at 25° C. to 30° C. and filtered to give 5.0 gm of tolterodine tartrate form I.

EXAMPLE 2

Tolterodine free base (5.0 gm) is dissolved in acetone (80 ml) and tartaric acid (3.0 gm) is added to the solution. Then the contents are stirred for 2 hours at 25° C. to 30° C. and filtered to give 5.0 gm of tolterodine tartrate form I.

EXAMPLE 3

Tolterodine free base (2.0 gm) is dissolved in ethyl acetate (25 ml) and tartaric acid (1.2 gm) is added to the solution. Then the contents are maintained for 2 hours at 25° C. to 30° C. and filtered to give 2.2 gm of tolterodine tartrate form II.

EXAMPLE 4

Tolterodine free base (2.0 gm) is dissolved in methyl tert-butyl ether (25 ml), tartaric acid (1.2 gm) is added and the reaction mass is heated to 40° C. Then the contents are cooled to 25° C., maintained for 2 hours at 25° C. to 30° C. and filtered to give 2.1 gm of tolterodine tartrate form III.

EXAMPLE 5

Tolterodine tartrate (2.0 gm), methanol (50 ml) and water (50 ml) are mixed. The solution is subjected to freeze drying for 20 hours to give 1.9 gm of tolterodine tartrate form IV.

EXAMPLE 6

Tolterodine tartrate (2.0 gm), ethanol (50 ml) and water (50 ml) are mixed. The solution is subjected to freeze drying for 20 hours to give 1.9 gm of tolterodine tartrate form IV.

EXAMPLE 7

Example 5 is repeated using tolterodine tartrate form I instead of tolterodine tartrate. The yield of tolterodine tartrate form IV is 1.9 gm.

EXAMPLE 8

Tolterodine tartrate (2.0 gm), methanol (50 ml) and water (50 ml) are mixed. The solvents are removed from the solution by vacuum drying for 10 hours at 60° C. to give 1.8 gm of amorphous tolterodine tartrate.

EXAMPLE 9

Example 8 is repeated using tolterodine tartrate form II instead of tolterodine tartrate. The yield of amorphous tolterodine tartrate is 1.8 gm.

EXAMPLE 10

Tolterodine tartrate (2.0 gm), methanol (50 ml) and water (50 ml) are mixed. The solution is subjected to spray drying in a Mini-Spray Dryer (Buchi Model-190) at an inlet temperature 89° C.-91° C. and outlet temperature 61° C.-42° C. to give 1.7 gm of amorphous tolterodine tartrate.

We claim:

1. A crystalline tolterodine tartrate form I, characterized by an x-ray powder diffraction spectrum having peaks expressed as 2θ at about 11.9, 13.6, 14.2, 15.9, 16.9, 18.4, 18.8, 20.4, 22.0, 23.9, 25.4, 26.3 and 29.8 degrees.

2. The crystalline tolterodine tartrate form I as defined in claim 1, further characterized by an x-ray powder diffraction spectrum as in FIG. 1.

3. The process for preparation of tolterodine tartrate form 1 as defined in claim 1, which comprises the steps of: a) dissolving tolterodine free base in a suitable solvent; b) adding tartaric acid; and c) isolating tolterodine tartrate form I; wherein the suitable solvent is selected from the group consisting of ethanol, methylene dichloride, chloroform, acetone, acetonitrile and 1,4-dioxane.

4. The process according to claim 3, wherein the suitable solvent is ethanol.

5. The process according to claim 3, wherein the suitable solvent is acetone.

6. A crystalline tolterodine tartrate form II, characterized by an x-ray powder diffraction spectrum having peaks expressed as 2θ at about 8.7, 9.0, 9.6, 10.1, 10.4, 11.9, 14.0, 15.7, 16.9, 17.6, 17.9, 18.4, 18.7, 20.0, 20.5, 22.1, 24.5, 29.1 and 35.9 degrees.

Figure 2:
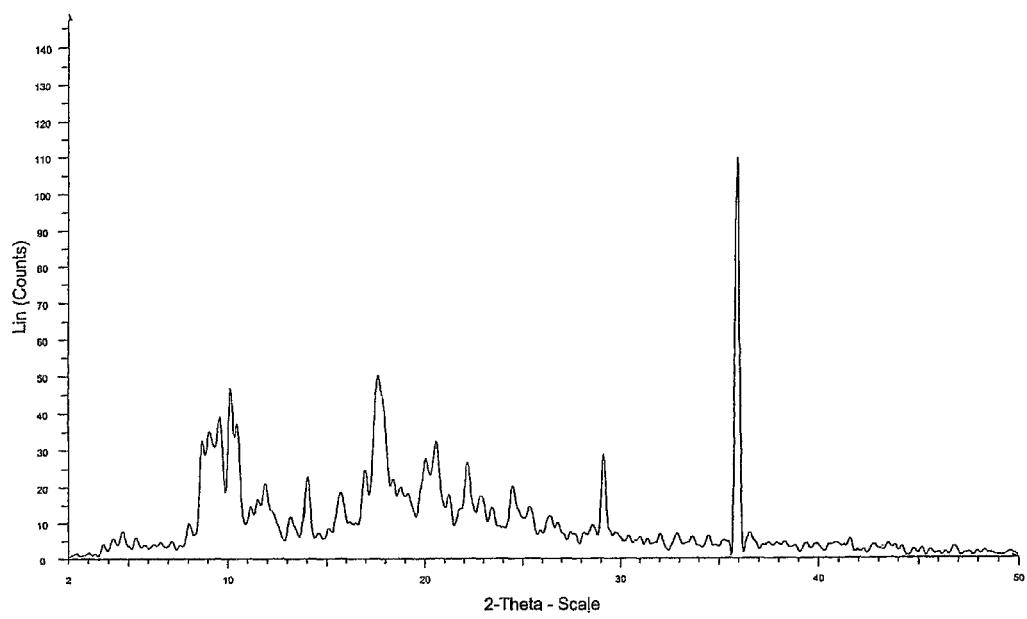
FIG. 2 is a x-ray powder diffraction spectrum of tolterodine tartrate form II.

7. The crystalline tolterodine tartrate form II as defined in claim 6, further characterized by an x-ray powder diffraction spectrum as in FIG. 2.

8. The process for preparation of tolterodine tartrate form II as defined in claim 6, which comprises the steps of: a) dissolving tolterodine free base in ethyl acetate; b) adding tartaric acid; and c) isolating tolterodine tartrate form II.

9. A crystalline tolterodine tartrate form III, characterized by an x-ray powder diffraction spectrum having peaks expressed as 2θ at about 9.1, 9.7, 10.6, 11.7, 11.9, 12.7, 14.3, 15.7, 17.9, 18.5, 18.8, 19.1, 20.1, 20.4, 22.1, 22.5, 25.1, 32.8 and 35.5 degrees.

Figure 3:
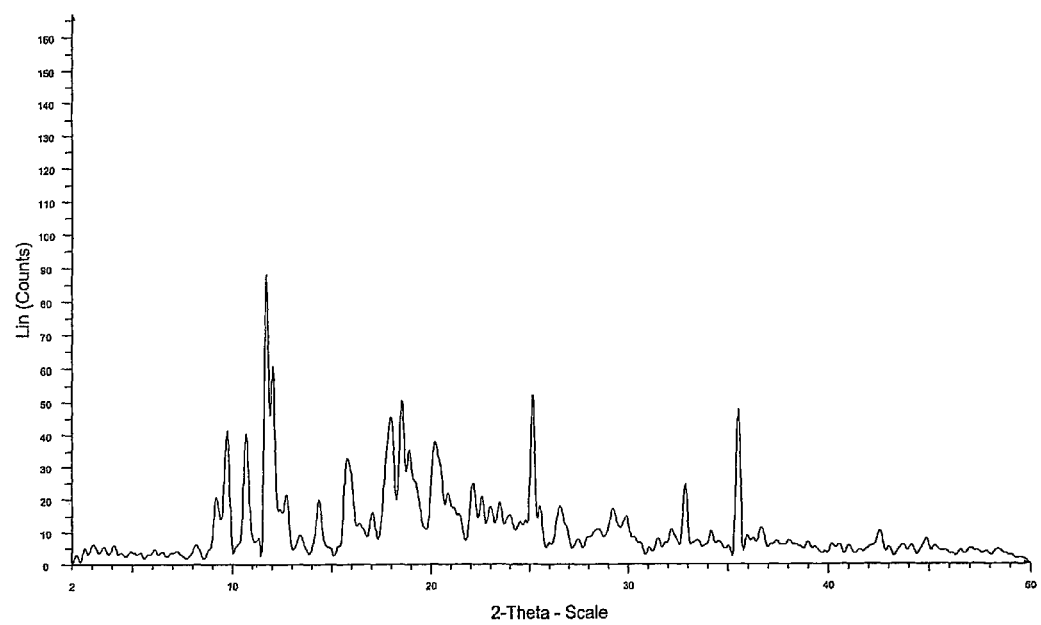
FIG. 3 is a x-ray powder diffraction spectrum of tolterodine tartrate form III.

10. The crystalline tolterodine tartrate form III as defined in claim 9, further characterized by an x-ray powder diffraction spectrum as in FIG. 3.

11. The process for preparation of tolterodine tartrate form III as defined in claim 9, which comprises the steps of: a) dissolving tolterodine free base in methyl tert-butyl ether; b) adding tartaric acid; and c) isolating tolterodine tartrate form III.

12. A crystalline tolterodine tartrate form IV, characterized by an x-ray powder diffraction spectrum having peaks expressed as 2θ at about 7.8, 9.8, 15.2, 17.2, 17.7, 18.4, 18.9, 20.3 and 25.9 degrees.

Figure 4:
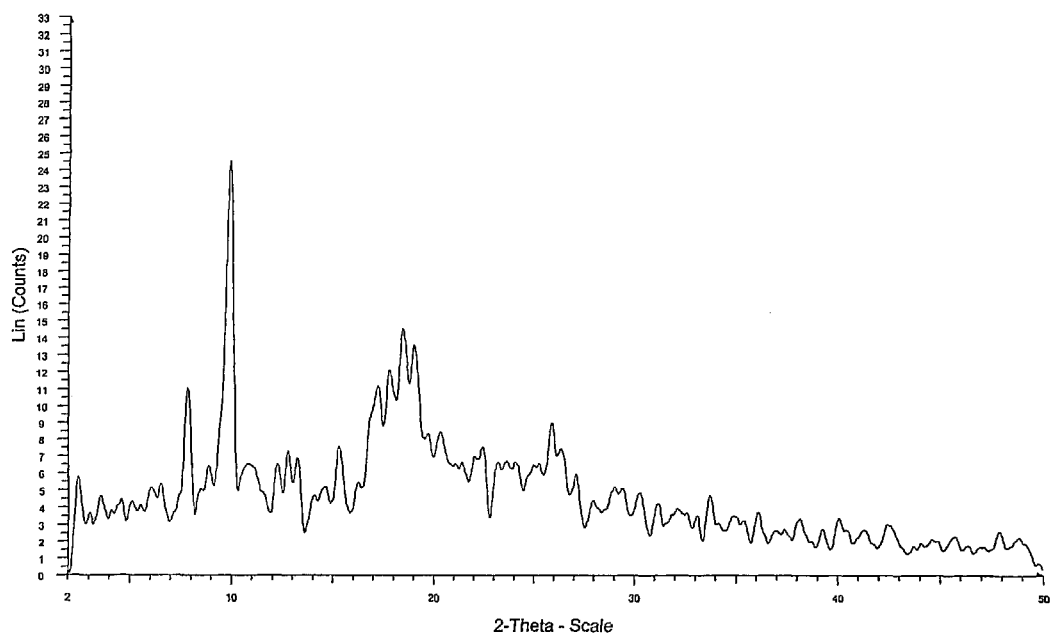
FIG. 4 is a x-ray powder diffraction spectrum of tolterodine tartrate form IV.

13. The crystalline tolterodine tartrate form IV as defined in claim 12, further characterized by an x-ray powder diffraction spectrum as in FIG. 4.

14. The process for preparation of tolterodine tartrate form IV as defined in claim 12, which comprises the steps of: a) mixing tolterodine tartrate, an alcohol and water; and b) removing the solvents from the solution formed in step (a) by freeze drying; wherein the alcohol is selected from the group consisting of methanol, ethanol, isopropyl alcohol and n-butanol.

15. The process according to claim 14, wherein the suitable alcohol is methanol.

16. The process according to claim 14, wherein the suitable alcohol is ethanol.

Figure 5:
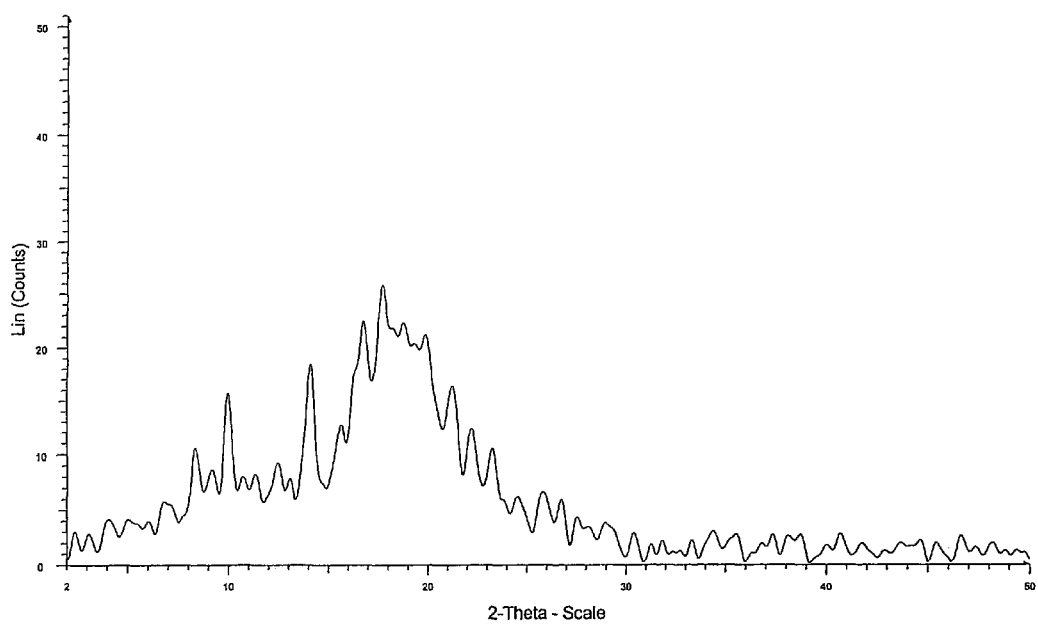
FIG. 5 is a x-ray powder diffraction spectrum of amorphous tolterodine tartrate.

17. Amorphous tolterodine tartrate characterized by an x-ray powder diffraction spectrum as in FIG. 5.

18. The process for preparation of amorphous tolterodine tartrate as defined in claim 17, which comprises the steps of: a) mixing tolterodine tartrate, an alcohol and water; and b) removing the solvents from the solution formed in step (a) by vacuum drying or by spray drying; wherein the alcohol is selected from the group consisting of methanol, ethanol, isopropyl alcohol and n-butanol.

19. The process according to claim 18, wherein the suitable alcohol is methanol.

20. The process according to claim 18, wherein the suitable alcohol is ethanol.

21. The process according to claim 18, wherein the solvents are removed by vacuum drying.

22. The process according to claim 18, wherein the solvents are removed by spray drying.

23. A pharmaceutical composition comprising a polymorphic form of tolterodine tartrate and a pharmaceutically acceptable carrier or diluent.

24. A pharmaceutical composition comprising a polymorphic form of tolterodine tartrate as claimed in claim 1 and a pharmaceutically acceptable carrier or diluent.

25. A pharmaceutical composition comprising a polymorphic form of tolterodine tartrate as claimed in claim 6 and a pharmaceutically acceptable carrier or diluent.

26. A pharmaceutical composition comprising a polymorphic form of tolterodine tartrate as claimed in claim 9 and a pharmaceutically acceptable carrier or diluent.

27. A pharmaceutical composition comprising a polymorphic form of tolterodine tartrate as claimed in claim 12 and a pharmaceutically acceptable carrier or diluent.

28. A pharmaceutical composition comprising a polymorphic form of tolterodine tartrate as claimed in claim 17 and a pharmaceutically acceptable carrier or diluent.

* * * * *